US 6,383,488 B1

(12) United States Patent
Ramudo et al.

(10) Patent No.: US 6,383,488 B1
(45) Date of Patent: May 7, 2002

(54) PRE-M/M EPITOPES OF DENGUE VIRUS, SYNTHETIC PEPTIDES, CHIMERIC PROTEINS AND THEIR USE

(75) Inventors: Susana Vazquez Ramudo; Guadalupe Guzman Tirado; Gerardo Enrique Guillen Nieto; Orlando Luis Pardo Lazo; Glay Chinea Santiago; Ana Beatriz Perez Diaz; Maritza Pupo Antunez; Rosmari Rodriguez Roche; Osvaldo Reyes Acosta; Hilda Elisa Garay Perez; Gabriel Padron Palomares; Maylin Alvarez Vera; Luis Morier Diaz; Omaida Perez Insuita; Jose Luis Pelegrino Martinez De La Cotera, all of Habana (CU)

(73) Assignees: Centro de Ingeniera Genetic Y Biotechnologies (CIGB); Instituto de Medicina Tropical "Pedro Kouri", both of Habana (CU)

( * ) Notice: Subject to any disclaimer, the term of this patent is extended or adjusted under 35 U.S.C. 154(b) by 0 days.

(21) Appl. No.: 09/341,833

(22) PCT Filed: Jan. 13, 1998

(86) PCT No.: PCT/CU98/00001

§ 371 Date: Oct. 14, 1999

§ 102(e) Date: Oct. 14, 1999

(87) PCT Pub. No.: WO98/31814

PCT Pub. Date: Jul. 23, 1998

(30) Foreign Application Priority Data

Jan. 15, 1997 (CU) ................................................ 13/97

(51) Int. Cl.[7] .......................... A61K 39/12; A61K 39/00; A61K 39/395; A61K 39/385; A61K 39/193

(52) U.S. Cl. ................................ 424/186.1; 424/184.1; 424/185.1; 424/130.1; 424/193.1; 424/204.1; 424/218.1; 530/324; 530/323; 530/350

(58) Field of Search ............................ 424/130.1, 184.1, 424/185.1, 186.1, 193.1, 206.1, 218.1; 530/324, 323, 350

(56) References Cited

FOREIGN PATENT DOCUMENTS

| CU | 0 474 313 A2 | 11/1992 |
|---|---|---|
| WO | WO-96/40933 A1 * | 12/1996 |

OTHER PUBLICATIONS

Murray et al; Processing of the dengue virus . . . ; J. Gen. Vir.; vol. 74; pp. 175–182, 1993.*
Randolph et al.; Acidotropic amines inhibit proteolytic . . . ; Vir; vol. 174; pp. 450–458, 1990.*

(List continued on next page.)

Primary Examiner—Hankyel T. Park
Assistant Examiner—Stacy S. Brown
(74) Attorney, Agent, or Firm—Hoffmann & Baron, LLP

(57) ABSTRACT

The present invention relates to five synthetic peptides of pre-M/M protein of Dengue-2 virus, corresponding to amino acid sequences 3–31, 45–67, 57–92, 69–93 and 103–124. The anti-peptide immune response was evaluated in mice. Recombinant fusion proteins were also obtained, including regions of pre-M/M protein. The presence of B cell epitopes in both mice and humans was demonstrated in the pre-M/M protein peptides. Peptides 3–31 and 103–124 elicited neutralizing antibodies against the four serotypes of Dengue virus. Virus-specific proliferative responses were demonstrated in mice immunized with non-conjugated peptides 3–31 and 57–92. Mice immunized with conjugated peptides 3–31, 57–92, and 69–93 were protected when they were challenged with Dengue-2 virus. Thus, the presence of sequential epitopes in Pre-M/M protein of Dengue-2 virus was demonstrated, as well as their relevance in the immune response against this flavivirus.

6 Claims, 11 Drawing Sheets

OTHER PUBLICATIONS

Figure 1A:
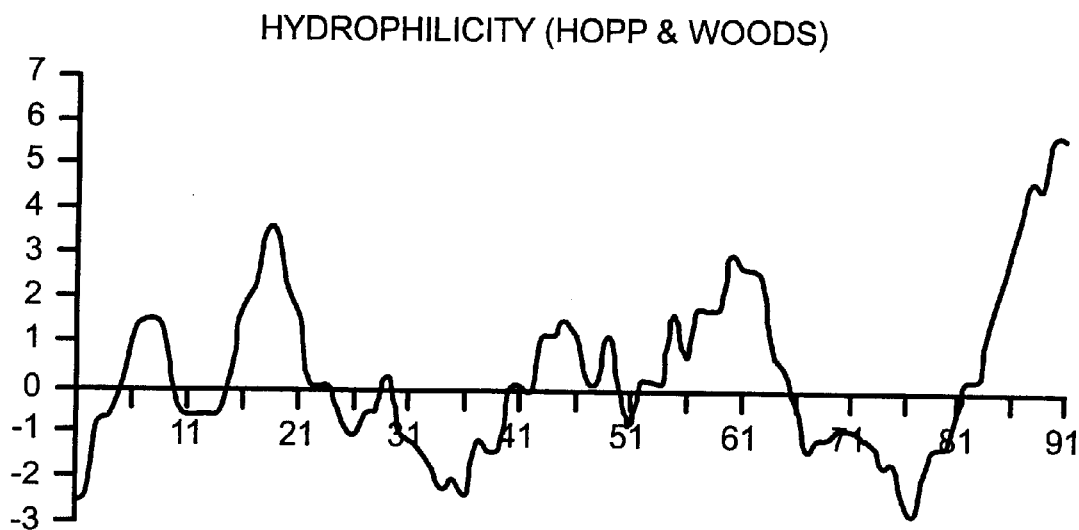
Figure 1B:
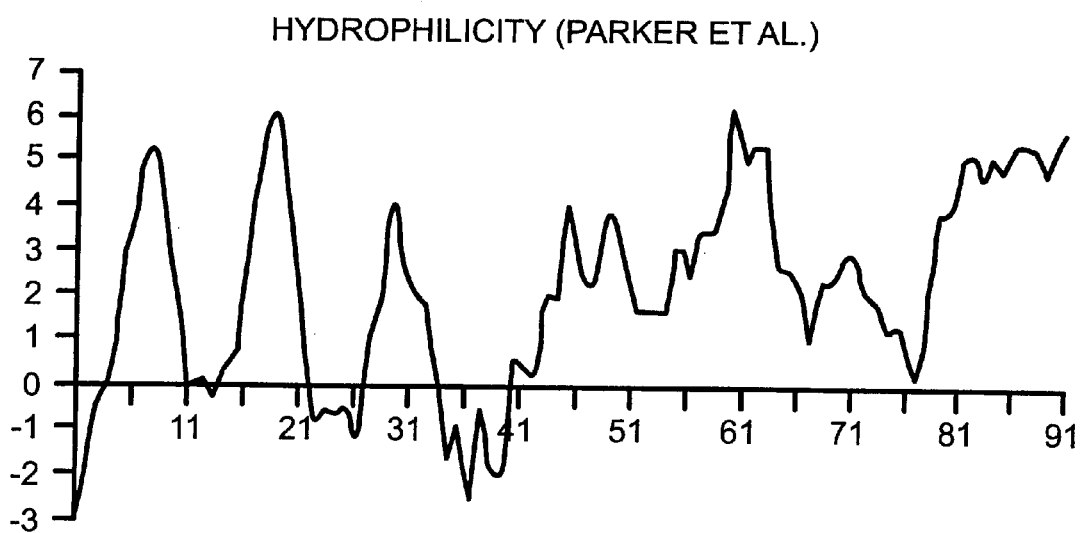
Figure 1C:
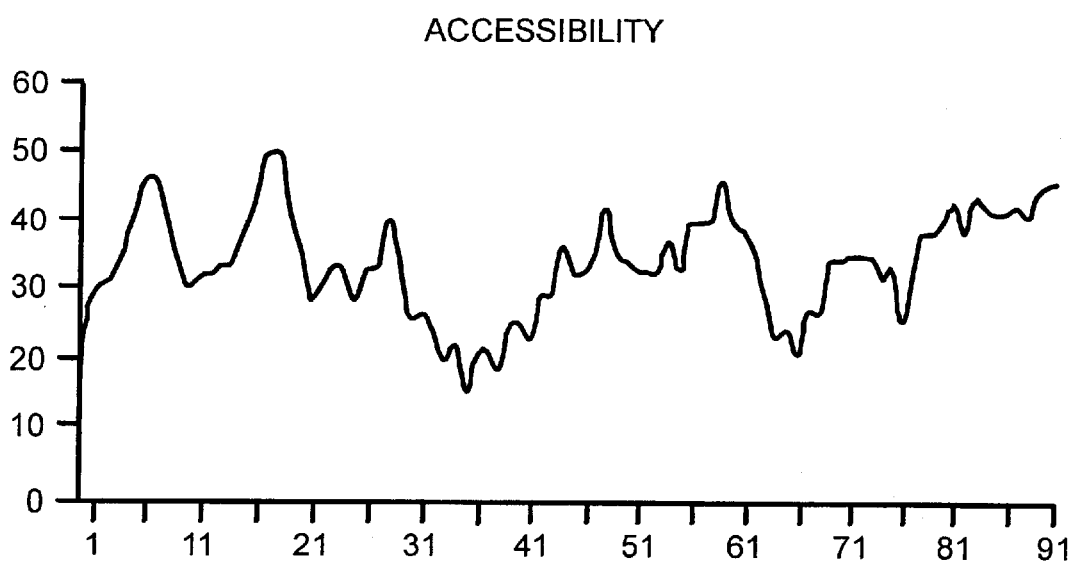
Figure 1D:
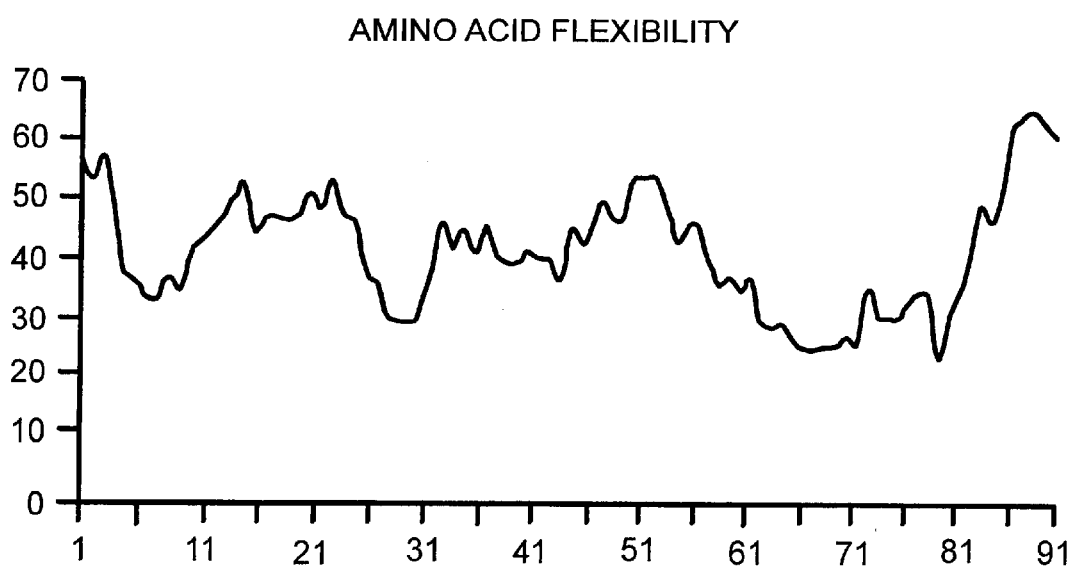
Figure 1E:
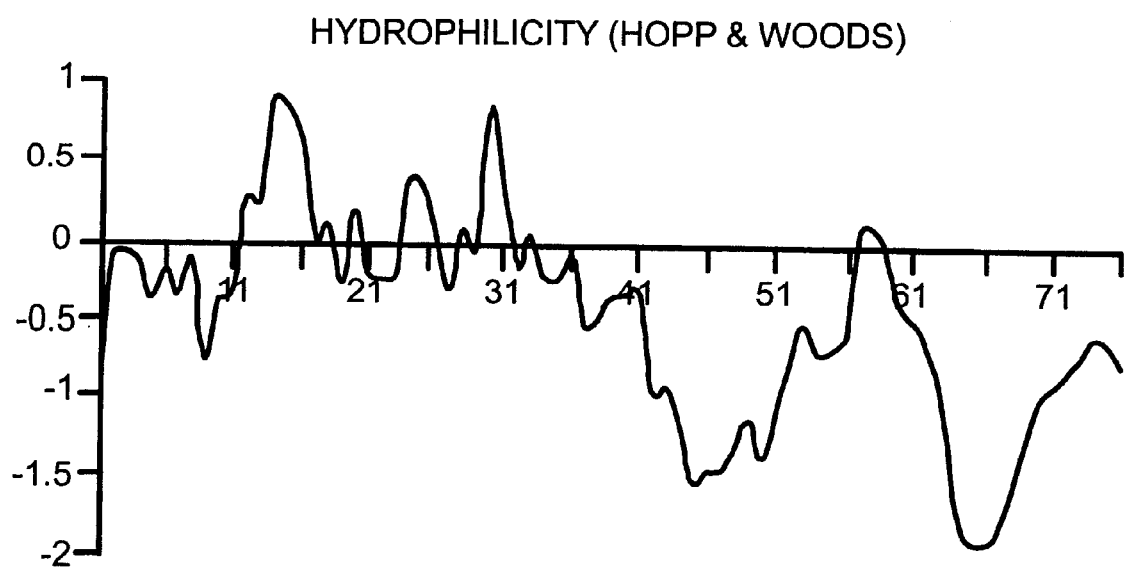
Figure 1F:
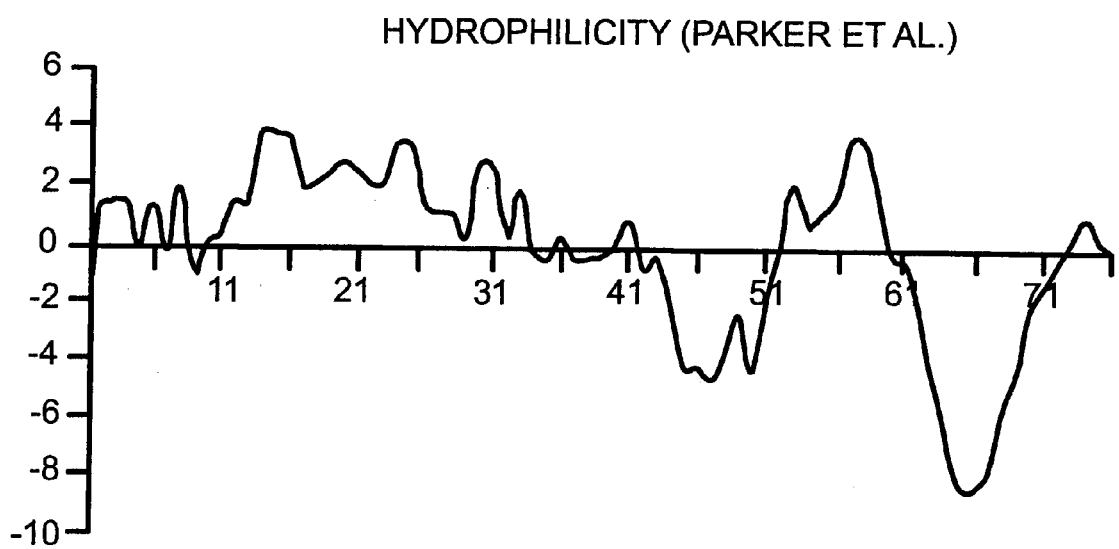
Figure 1G:
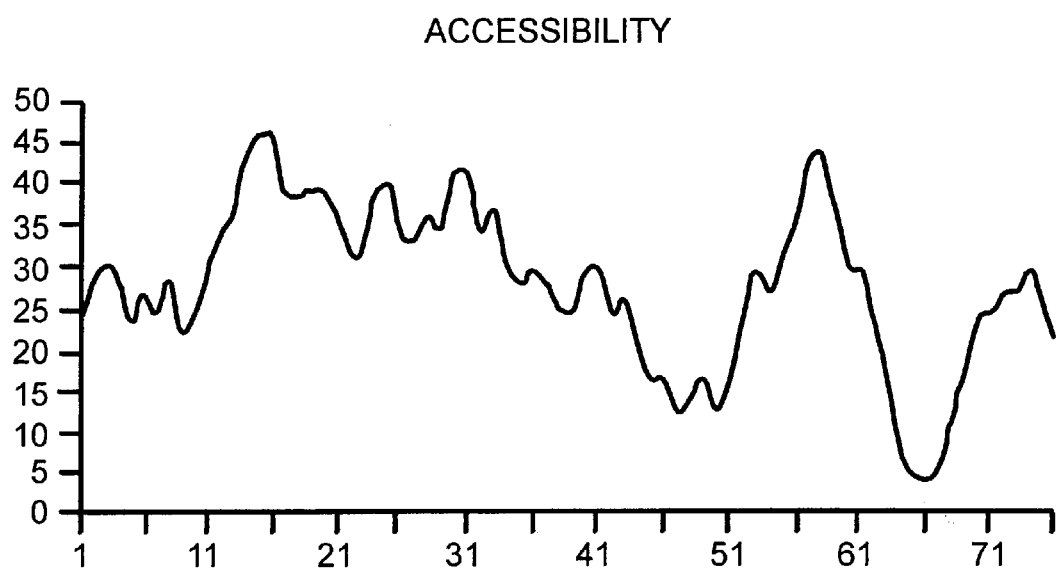
Figure 1H:
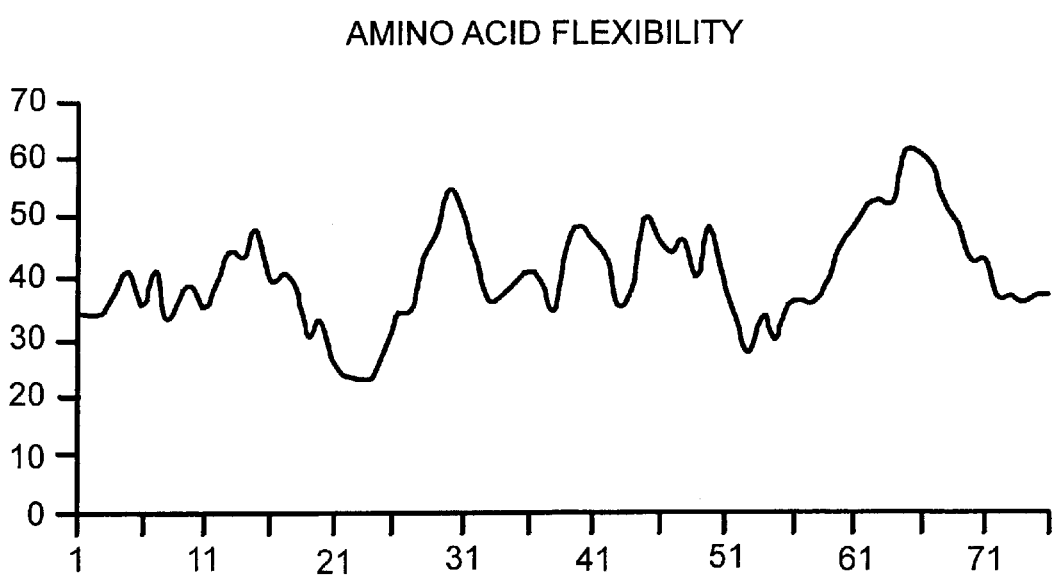
Figure 5:
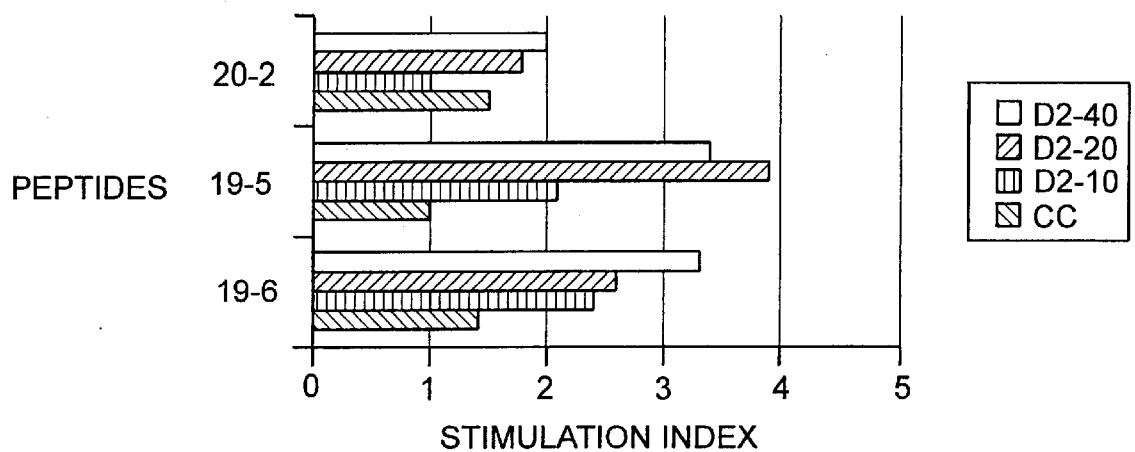

Irie et al., "Sequence analysis of cloned dengue virus type 2 genome (New Guinea–C strain)", Department of Biochemistry and Molecular Biology, University of Kansas Medical Center, *Gene* 75 197–211 (1989).

Gruenberg et al., "Partial Nucleotide Sequence and Deduced Amino Sequence of the Structural Proteins of Dengue Virus Type 2, New Guinea C and PUO–218 Strains", *J. gen Virol.* 69, 1391–1398 (1988).

Zhao et al., "Cloning Full–Length Dengue Type 4 Viral DNA Sequences: Analysis of Genes Coding for Structural Proteins", *Virol.* 155:77–88 (1986).

Gaines et al., "Pathogen–Derived Resistance to Dengue Type 2 Virus in Mosquito Cells by Expression of the Premembrance Coding Region of the Viral Genome", *Journal of Virology*, p. 2132–2137 (1996).

Kaufman et al., "Monoclonal Antibodies for Dengue Virus PRM Glycoprotein Protect Mice Against Lethal Dengue Infection", *Am. J. Trop. Med. Hyg.*, 41(5), pp. 576–580 (89–157) 1989.

Bray et al., "Dengue Virus Premembrane and Membrane Proteins Elicit a Protection Immune Response", *Virology*, 185, 505–508 (1991).

* cited by examiner

```
                 .........1.........2.........3.........4.........5.........6
      AA (pre)  |FHLTTRGGEPTLIVSKQERGKSLLFKTSAGVNMCTLIAMDLGELCEDTMTYKCPRMTEAE|
      PHD sec   | EEEE    EEEEEEEE     EEEE      EEEEEEE       EEEEEE   EEEE |
      SUB sec   |LEE...LL.EEEEEEE..LL.EEEEE.LLLL.EEEEEE.LLLL..L.L.EE..LLLLLLL|
ACCESSIBILITY
      P_3 acc   |eebeeeebee bbbeeeeebeebbbebeebebbbbbbbbebbeebbebebbebeeee|
      SUB acc   |.e...ee.e..b.b..eee.e....e....b.b..b..bbe..b..b.e.eee.|

.........7.........8.........9........10........11......1
      AA (pre)  |PDDVDCWCNATDTWVTYGTCSQTGEHRRDKR|
      PHD sec   |    E     EEEEEEE              |
      SUB sec   |LLL.....LL.EEEEEEE...LLLLLL.LLL|
ACCESSIBILITY
      P_3 acc   |eeebbbbbeeeebbbbbebeeeeeeeeee|
      SUB acc   |.e.b.bbbe.ee..b..b.b.eeeee..eee|
```

FIG. 2A

FIG. 2B

```
            ......,....1....,....2....,....3....,....4....,....5....,....6
   AA (M)   |SVALDPHVGLGLETRTETWMSSEGAWKQIQKVETWALRHPGFTVIGLFLAHAIGTSITQK|
   PHD sec             HHH HHHHHHHHHHHHHHH              HHHHHHHHHH      HHHH
   SUB sec  |L....LLLLLLL..L.....L.HHHHHHHHHHHHHHHH.L.HHHHHHHHHHHHLL.HHHH|
ACCESSIBILITY
   P_3 acc  |ebbbbebbebbbee  eeebbebeebeeeebeeb  bbbb   bebbbbbbbbbbbee  bbe|
   SUB acc  |e..b........e..e..e..b..eeb.e....b..bb.....b..bb......b.bbbbbb..bb.e...|

......,....7....,....8....,....9....,....10...,....11...,....1
   AA (M)   |GIFILLMLVTPSMAM|
   PHD sec  |HHHHHHHHHHHH   |
   SUB sec  |HHHHHHHHH....LLL|
ACCESSIBILITY
   P_3 acc  |bbbbbbbbbbbbebee|
   SUB acc  |.bbbbbbbbb......|
```

FIG. 3A
DENGUE PRE-VARIABILITY

FIG. 3B
MBV PRE-VARIABILITY

FIG. 3C
FLAVIVIRUS PRE-VARIABILITY

FIG. 3D DENGUE M VARIABILITY

FIG. 3E MBV M VARIABILITY

FIG. 3F FLAVIVIRUS M VARIABILITY

FIG. 4A

```
              10        20        30        40        50        60
AA       FHLTTRNGEPHMIVMRQEKGKSLLFKTGDGVNMCTLMAMDLGELCEDTITYKCPLLRQNE
AMPHI 7                                 ++++++++  ++++++   
AMPHI 11                                +++++++  +++++++   
RT 4     ++++                                        ++++
RT 5     +++++                                       ++++

70        80        90
AA       PEDIDCWCNSTSTWVTYGTCTTTGEHRREKR
AMPHI 7
AMPHI 11                    +++
RT 4
RT 5
```

FIG. 4B

```
              10        20        30        40        50        60
AA       SVALVPHVGMGLETRTETWMSSEGAWKHAQRIETWILRHPGETIVAAILAYTIGTTHFQR
AMPHI 7                           ++++++                ++++
AMPHI 11              +++++       ++++                  ++++    ++++
RT 4
RT 5

70
AA       ALIFILLTAVAPSMT
AMPHI 7
AMPHI 11
RT 4
RT 5
```

PRE-M/M EPITOPES OF DENGUE VIRUS, SYNTHETIC PEPTIDES, CHIMERIC PROTEINS AND THEIR USE

CROSS REFERENCES TO RELATED APPLICATIONS

This application is a 371 national stage entry of PCT/CU98/00001 filed Jan. 13, 1998.

FIELD OF THE INVENTION

The present invention is in the field of biotechnology and relates to recombinant DNA techniques, in particular to the production of synthetic peptides coding for pre-M/M protein of Dengue virus serotype 2 and chimeric proteins which contain epitopes of pre-M/M protein of Dengue virus serotype 2 and 4.

The technical objective is to identify Pre-M/M neutralizing and protective epitopes, cross reactive for all dengue virus serotypes to obtain an immunogen for human vaccination.

BACKGROUND

Dengue virus belongs to the Flavivirus genus, family Flaviviridae (Westaway, E. G. et al. 1985. Flaviviridae. Interviol. 24 p.183). It is an enveloped virus with a single RNA chain of positive polarity as genetic material, which codes for a polyprotein processed co- and post-transductionally by cellular and viral proteases.

There are two structural proteins in the viral membrane: E (envelope) and M (membrane), while there are several copies of the other structural protein, C (capside) forming the isometric nucleocapside. Besides, at least seven non-structural proteins have been identified (NS1, NS2a, NS2b, NS3, NS4a, NS4b, NS5).

Glycoproteins E and NS1 are individually able to offer active and passive protection against the homologous serotype of Dengue virus, while the highly conformational complexity of the relevant epitopes is preserved. For this reason, recombinant eukaryotic cellular systems have been mainly selected for the immunological evaluation of these proteins, for example vaccinia virus (Bray, M. et al. 1989. Mice immunized with recombinant Vaccinia virus expressing dengue-4 structural proteins with or without nonstructural protein NS1 are protected against fatal dengue virus encephalitis. J. Virol. 63 p.2853) and baculovirus (Zhang, Y. M. et al. 1988. Immunization of mice with dengue structural proteins and nonstructural protein NS1 expressed by baculovirus recombinant induces resistance to dengue virus encephalitis. J. Virol. 62 p.3027).

The small protein M (8 kDa) is synthesized like a glycosylated precursor named pre-M (22 kDa approximately), which suffers a late endoproteolitic cleavage just before or after the liberation of the virus of the infected cell (Murray, J. M. et al. 1993. Processing of the dengue virus type 2 proteins prM and C-prM. J. Gen. Virol. 74 p.175). The cleavage, which is probably done by a cellular protease, seems to happen in the post-Golgi acidic vesicles, being inhibited by agents that destabilized the low pH of this vesicles (Randolph, V. B. et al. 1990. Adidotropic amines inhibit proteolytic processing of Flavivirus prM protein. Virol. 174 p.450). The fragment pre- has been identified in vitro only in the extracellular medium, its destiny in vivo remains unknown (Murray, J. M. et al. 1993. Processing of the dengue virus type 2 proteins prM and C-prM. J. Gen. Virol. 74 p.175).

It is thought that the function of pre-M/M during the Flavivirus exocytic via is to avoid the activation of the fusogenic membrane domain of E with the acidic pH of the environment (Randolph, V. B. et al. 1990. Acidotropic amines inhibit proteolytic processing of Flavivirus prM protein. Virol. 174 p.450); if this event happens, then the viral liberation will be prevented. In fact, it has been determined that pre-M and E interact in the immature intracellular virions (Wengler, G. y Wengler, G. 1989. Cell-associated West Nile flavivirus is covered with E+pre-M protein heterodimers which are destroyed and reorganized by proteolytic cleavage during virus release. J. Virol. 63 p.2521), and that the native conformation of E it is only acquired in the presence of pre-M (Konishi, E. y Mason, P. W. 1993. Proper maturation of the Japanese encephalitis virus envelope glycoprotein requires cosynthesis with the premembrane protein. J. Virol. 67 p.1672). In addition, already liberated virions that only have pre-M in their membranes show, in general, a lower infectivity than the completely mature virion (Wengler, G. y Wengler, G. 1989. Cell-associated West Nile flavivirus is covered with E+pre-M protein heterodimers which are destroyed and reorganized by proteolytic cleavage during virus release. J. Virol. 63 p.2521), in which although M and pre-M are present, the former is predominant.

Pre-M and M offer an active protection when they have been expressed in recombinant vaccinia virus, but this do not happen with the fragment pre- (Bray, M. y Lai, C.-J. 1991. Dengue virus premembrane and membrane proteins elicit a protective immune response. Virol. 185 p.505), besides the combination pre-M or M with glycoprotein E in the same recombinant Vaccinia virus gives in general levels of protection higher than those reached by each protein individually. Similarly, certain antibodies against pre-M/M are able to protect passively in mice (Kaufman, B. M. et al. 1989. Monoclonal antibodies for dengue virus prM glycoprotein protect mice against lethal dengue infection. Am J. Trop. Med. & Hyg. 41 p.576).

The use of synthetic peptides has allowed to establish the molecular basis of antigenicity according to spacial conformation and the immunological properties of the antigen involved [Arnon, R. y Sela, M. 1985. Synthetic Vaccines: present and future. Ann. Inst. Pasteur/Immunol 136 D, 271–282]. The synthetic peptides as anti-dengue vaccine subunits will allow to include in the final formulation only the protective epitopes that do not cause immune-amplification (Halstead, S. B., y O'Ruourke, E. J. 1977. Dengue viruses and mononuclear phagocytes. I. Infection enhancement by non-neutralizing antibody. J. Exp. Med. 146 p.201; Halstead, S. B. 1979. In vivo enhancement of dengue virus infection in rhesus monkeys by passively transferred antibody. J. Infect. Dis. 140 p.527), or alternatively, to include protective peptides of each of the four serotypes. The characterization of the antigenic determinants of E and NS1 has been carried out successfully. However, there are no similar studies on the also important protein pre-M/M, that is why the results of this paper are a first step on that direction.

The efforts to express the flaviviral protein pre M, M and E in *E. coli* have not always been successful (Chambers, T. J. et al. 1990. Production of yellow fever virus proteins in infected cells: identification of discrete polyprotein species and analysis of cleavage kinetics using region-specific polyclonal antiserum. Virol. 177 p.159; Yan, B.-S. et al. 1994. Truncating the putative membrane association region circumvents the difficulty of expressing hepatitis C virus protein E1 in *Escherichia coli*. J. Virol. Meths. 49 p.343).

Apparently, the hydrophobic regions these protein have in C-terminal are the cause of the low or undetectable heterologous expression levels (Yan, B.-S. et al. 1994. Truncating the putative membrane association region circumvents the difficulty of expressing hepatitis C virus protein E1 in Escherichia coli. J. Virol. Meths. 49 p.343).

The expression of those proteins (as well as NS1) in E.coli, in general have been obtained by fusion (fragmented or not) to other bacterial proteins (e.g. b -galactosidase (Cane, P. A. y Gould, E. A. 1988. Reduction of yellow fever mouse neurovirulence by immunization with a bacterially synthesized non-structural protein (NS1) fragment. J. Gen. Virol. 69 p.1241), TRPE (Megret, F. et al. 1992. Use of recombinant fusion proteins and monoclonal antibodies to define linear and discontinuous antigenic sites on the Dengue envelope glycoprotein. Virol. 187 p.480) and the protein A of Staphylococcus aureus (Murray, J. M. et al. 1993. Processing of the dengue virus type 2 proteins prM and C-prM. J. Gen. Virol. 74 p.175). In these fusion proteins most of the relevant conformational epitopes are absent, because though the antisera generated against them can recognize the whole virus, they are not able neither to neutralize it nor to inhibit their hemagglutinating properties (Megret, F. et al. 1992. Use of recombinant fusion proteins and monoclonal antibodies to define linear and discontinuous antigenic sites on the Dengue envelope glycoprotein. Virol. 187 p.480). However, recent reports show that the solubility of the fusion proteins, and as a consequence, the use of non-denaturalizing methods for its purification, may preserve most of the neutralizing (Seif, S. A. et al. 1995. Finer mapping of neutralizing epitope(s) on the C-terminal of Japanese encephalitis virus E-protein expressed in recombinant Escherichia coli system. Vaccine 13 p.1515) and protective (Srivastava, A. K. et al. 1995. Mice immunized with a dengue type 2 virus E and NS1 fusion protein made in Escherichia coli are protected against lethal dengue virus infection. Vaccine 13 p.1251) epitopes they possess.

In the case of pre-M/M, its pre-domain has 6 cysteines involved in 3 disulfide bridges, as well as an N-glycosylation site in the asparagine 69. The structure of E and NS1 is even more complicated; it involves 6 disulfide bridges and several N-glycosylation sites. However, the little ectodomain of M is apparently free of those conformational complexities because it does not have cysteines, and it is not glycosylated in its natural form.

The insertion of heterologous fragments in permissive areas of immunogenic proteins which topology is more or less known and immunization of these fusions is a complementary alternative to the use of synthetic peptides. Both strategies allow defining the presence of sequential B cell, as well as T cell epitopes. The biological importance of these epitopes could be experimentally evaluated to decide where to include them or not in certain vaccine preparation.

SUMMARY OF THE INVENTION

The invention, provides synthetic peptides of Dengue virus preM/M protein comprising amino acids 3–11 (Sequence ID No.:1), 45–67 (Sequence ID No.:2), 57–92 (Sequence ID No.:3) 69–93 (Sequence ID No.:4) and 103–124 (Sequence ID No.:5) that include at least one opitope that is cross reactive with any Dengue virus serotype; and mimetic compounds thereof.

Also provided are diagnostic tests and pharmaceutical formulations that include the above peptides or mimetic compounds useful in the detection and prophylaxis or treatment of flavivirus infections.

The invention further provides antibodies and antibody fragments that specifically bind the Dengue virus preM/M protein comprising amino acids 3–31 (Sequence ID No.:1), 45–67 (Sequence ID No.:2), 57–92 (Sequence ID No.:3), 69–93 (Sequence ID No.:4) and 103–124 (Sequence ID No.:5) that include at least one epitope that is cross reactive with any Dengue virus scrotype. Vaccine and therapeutic preparations that include these antibodies are also provided.

Further, the invention provides genetic constructs that include amino acid sequences that include epitopes of pre-M/M from Dengue virus scrotypes 2 and 4, fused to a carrier protein.

DETAILED DESCRIPTION OF THE INVENTION

Five peptides from Pre-M/M protein of Dengue 2 virus which cover 58% of the aminoacid sequence (97/166 AA) were chemically synthesized. They were 3–31; 45–67; 57–92; 69–93; and 103–124, which were subsequently named B 19-6; B 20-2; B 19-5; B 20-1; B 20-3 respectively.

Peptides were inoculated in Balb/c mice both conjugated or not to a carrier protein. The sera obtained after immunization with the conjugated peptides were tested by in vitro neutralization by reducing the number of plaques and by ELISA. We also studied the active protection against a Dengue 2 viral challenge in the immunized mice.

In the case of mice immunized with the non-conjugated peptides, the antibody response was evaluated by ELISA and the proliferative response of spleen T lymphocytes against Dengue 2 virus was evaluated too. Fusion proteins were also obtained, and two of the four regions covered by peptides (1–42 and 92–133) were inserted to them and were expressed in E.coli bacteria. Immunization with these fusions will complement the results obtained with the synthetic peptides.

The presence of B cell epitopes in both mice and humans was demonstrated as the peptides were recognized by antibodies from the immunized mice and by sera from patients who had the clinical and serological diagnosis of Dengue virus, using ELISA in both cases. Peptides 19-6 and 20-3 were able to induce neutralizing antibody production against the four Dengue virus serotypes.

Virus-specific proliferative responses were demonstrated in mice immunized with non-conjugated peptides 19-6 and 19-5. Mice immunized with conjugated peptides 19-6, 20-1, and 19-5 showed a statistically significant level of protection when they were challenged with Dengue 2 virus.

Thus, the presence of sequential epitopes in Pre-M/M protein of Dengue virus 2 was demonstrated, as well as their relevance in the immune response against these flaviviruses.

EXAMPLES

Example 1

Prediction of Antigenic Regions and of T-cells Epitopes of Pre-M/M Protein of Dengue Virus Different theoretical methods were applied to predict the antigenic regions in the pre-M/M protein of D2 virus. These regions are those more likely to be recognized by antibodies obtained against the viral proteins, as well as to generate antibodies that recognized the original proteins. Some methods to predict T-cell epitopes were applied. Five initial peptides that have possible B- and T-cell epitopes were found (4 in pre- and 1 in M). The study of the antigenic structure of these proteins and the experimental determination of possible immunologically important peptides was based on this finding.

1.1 Predictions of Humoral Amino Acid

Methods used to predict the antigenicity were based on the aminoacidic sequence, since neither the three dimensional structure of the pre-M/M protein of Dengue virus has been determined experimentally, nor is there a significant similarity at sequence level with any protein of known three dimensional structure.

The A 15 strain of Dengue 2 isolated in Cuba in 1981 (Kour, G. et al. 1986. Hemorrhagic dengue in Cuba: history of an epidemic. Bull. P.A.H.O 20 p.24) was used to accomplish this example. The potentially antigenic regions were selected according to the following criteria:

a) regions of high antigenic propension according to different prediction methods based on hydrophilicity (Hoop, T. P. y Woods, K. R. 1981. Prediction of protein antigenic determinants from amino acid sequences. Proc. Natl. Acad. Sci. USA 78 p.3824; Parker, J. M. R. et al. 1986. New hydrophility sale derived from HPLC peptide retention data: correlation of predicted surface residues with antigenicity and X-ray derived accessible sites. Biochemistry 25 p.5425), flexibility (Karplus, P. A. y Schultz, G. E. 1985. Prediction of chain flexibility in proteins. A tool for the selection of peptide antigens. Naturwissenschaften 72 p.212) and accessibility (Emini, E. A. et al. 1985. Induction of hepatitis A virus-neutralizing antibody by a virus specific synthetic peptide. J. Virol. 55 p.836).

b) regions with high possibility of forming loops and turns according to predictions of secondary structure that use PHD (Rost, B. y Sander, C. 1993. Prediction of protein secondary structure at better than 70% accuracy. J. Mol. Biol. 232 p.584; Rost, B. y Sander, C. 1994. Combining evolutionary information and neural networks to predict protein secondary structure. Proteins 19 p.55; Rost, B. y Sander, C. 1994. Conservation and prediction of solvent accessibility in protein families. Proteins 20 p.216).

c) regions of high variability that include or not insertion/suppressions in respect to other flaviviruses, as well as potential regions of glycosylation in other flaviviruses that are used or not in Dengue virus.

A. Antigenicity Profiles

FIG. 1 shows the profiles that are obtained when applying to the pre- and M segments 4 properties of the amino acids related to the antigenicity.

In the pre- region there are high hydrophilicity and accessibility values in the regions that have the residues 6–9, 16–21, 28–31, 42–47, 58–65 and 82–91. It is remarkable the existence of a vast hydrophobic region between the residues 41–76, which corresponds to the transmembrane helices that are thought not to be exposed to the immune system. In the little ectodomain of M (residues 1–40) the region of major hydrophilicity/accessibility goes between 13–31 amino acids, especially at its beginning (AA 13–16).

B. Predictions of Secondary Structure

FIG. 2 shows the predictions of secondary structure and accessibility of the pre- and M segments according to PHD program. The results of the predictions show that many potentially antigenic regions (according to the profiles of FIG. 1) are predisposed to form loops/b-turns with exposed residues in the surface of the protein. It is predicted the formation of transmembrane helices for the region between aminoacids 41–76 of protein M, and this matches with the hydrophobic character of this region and suggests that the antigenic peptides of M are mainly in the ectodomain (1–40).

a. Alignments of sequences of protein pre- and M of Dengue and other Flavivirus. Variability and glycosylation.

In general, regions that are not exposed to the solvent have a bigger conservation in the family of homologous proteins. Therefore, regions of higher variability have a higher probability to be exposed.

In the case of viruses, variability is also an escape mechanism for the immunological pressure; of course this does not exclude that some conserved regions might be antigenic or that there could be conserved regions in the surface.

The analysis of sequences of regions pre- and M of 15 isolates of the 4 serotypes of Dengue virus shows that at least the 69% of the residues are strictly conserved. The more important variable residues are in the positions 28–30, 55–59, 69–72 and 80–83 of pre-, as well as in 27–30 of M. In general; these zones match the maximum of antigenic profiles of FIG. 1.

The comparison of the sequences of these regions in more than 30 flaviviral isolates shows that the region 1–33 of pre is highly variable, with possible loops predisposed to insertions/suppressions (in the positions 8 and 30) and several potential sites of N-glycosylation. On the contrary, the variability is lower in the domain 33–91 of pre-; there are several positions strictly conserved in all flaviviruses, for example: 6 cysteins forming of 3 disulfide bridges, at least 5 add residues in the region 4045, as well as the basic sequence 87–91, after which the endoproteolytic cleavage occurs just before or during the liberation of the mature virus. (FIG. 3)

Asn-69, conserved residue in the antigenic Dengue complex has the only N-glycosylation of pre-M/M protein of the complex. However, in the Flaviviridae family this region is in a possible exposed loop of high variability. At the same time the pre-M/M residues of Dengue virus that match the potential N-glycosylation sites in other Flavivirus (for example, AA 14 in JE, SLE, MVE YF and AA 32 in LI, LAN, YF TBE) are b-turns close to zones considered as antigenic.

1.2 Prediction of T Cell Epitopes

The prediction was done by two independent methods: the Rothbard and Taylor pattern method (Rothbard, J. B. y Taylor, W. R. 1988. A sequence pattern common to T-cell epitopes. EMBO J. 7 p.93.) and the determination of fragments with propensity to form alpha-helix structures (AMPHI 7 and 11) (Margalit, H. et al. 1987. Prediction of immunodominant helper T cell antigenic sites from the primary sequence. J. Immunol. 138 p.2213.). Results are shown in FIG. 4.

1.3 Peptides Proposed for the Identification of Relevant Epitopes

The determination of neutralizing and protective peptides in general is very important for the development of more efficient vaccines, and peptides from regions of high antigenic propension are very useful for their identification; especially of those of linear nature.

Table 1 shows a set of peptides that include regions predisposed to have B and T cell epitopes (according to the several predictive methods used in this example) of pre-M/M protein of D2 virus. If the validity of that prediction is demonstrated experimentally, the immunological important epitopes of each region will be placed accurately by the design of low size peptides in each of them.

TABLE 1

| Antigenic peptides proposed in pre-M/M protein of Dengue virus. |
|---|
| CODE |
| SEQUENCE |
| REGION |
| B 19-6 (SEQ ID NO: 1) |
| LTTRNGEPHMIVMRQEKGKSLLFKTGDGV |
| 3–31 |
| B 20-2 (SEQ ID NO: 2) |
| CEDTITYKCPLLRQNEPEDIDCW |
| 45–67 |
| B 19-5 (SEQ ID NO: 3) |
| RQNEPEDIDCWCNSTSTWVTYGTCTTTGEHRREKRS |
| 57–92 |
| B 20-1 (SEQ ID NO: 4) |
| NSTSTWVTYGTCTTTGEHRREKRSV |
| 69–93 |
| B 20-3 (SEQ ID NO:5) |
| LETRTETWMSSEGAWKHAQRIE |
| 103–124 |

Example 2

Chemical Synthesis of Oligopeptides and Oligonucleotides

1. Synthesis of Oligopeptides

All peptides were synthesized using a Boc-strategy in solid phase on the p-methyl-benzhydrilamine resin (resin MBHA, BACHEM, Switzerland).

The protected amino acids were offered by BACHEM. The protection of reactive groups of the amino acid chain was: Arg (Tos), Asp (OBzl), Cys (4-Me-Bzl), Glu (OBzl), Lys (2-CI-Z), Trp (CHO), Tyr (Cl2-Bzl), Thr (Bzl). Asn, Gin and Pro were used without protection in the lateral chains.

Discarding of the Boc-amino protective group was carried out using 37.5% trifluoracetic acid in dichloromethane. Activation with diisipropyl-carbodiimide (DIC) in situ was used for the coupling reaction of each residue, except for amino acids Asn and Gln, which were activated using DIC and 1-hydroxybenzotriazole in N,N-dimethylformide.

Final desprotection and peptide liberation of the resin was accomplished in special equipment. The procedure used is known as Low-High HF.

During the first part of the procedure (Low HF), the protected-resin system was treated with HF (25%): DMS (65%): p-cresol (10%) during 120 minutes at 0. The mixture was replaced by HF (25%): DMS (60%): EDT (10%): p-cresol (5%) in the case of Trp-containing peptides. Subsequently, the resin-peptide was washed several times with diethyl ether, dichloromethane and 2-propanol, and was vacuum-dried.

During the second part of the procedure (High HF), the resin-peptide was treated with HF (90%): anizole (10%) during 60 minutes at 0.

The raw product was washed with ether, then was extracted with 30% acetic in water and finally was lyophilized.

Peptides were characterized by RP-HPLC in a BAKER C-18 (4.6×100 mm) column and by spectrometry of masses using FAB as ionization method in a JEOL HX-110 HF equipment.

The aminoacidic sequence as well as its location in the preM-M protein of Dengue virus is shown in Table 1.

2.2. Synthesis of Oligonucleotides

Oligonucleotides were automatically synthesized in the equipment Gene Assembler Plus, according to the phosphoramidite method.

The sequence of the six oligonucleotides is shown in Table 2.

Table 2. Sites Xba I and EcoR I that are created in each end for its later manipulation are underlined and double-underlined, respectively. The reading frame of the codified protein is defined by the triplets of bases.

Oligonucleotide position

| Nucleotidic sequence |
|---|
| 1) 5' pre DEN-2 |
| 5'-TTT CTA GAT TTC CAT TTA ACC ACA CGT T-3' |
| 2) 3' pre DEN-2 |
| 5'-T TTC TAG ACC AAG GTC CAT GGC CAT GAG-3' |
| 3) 5' M DEN-2 |
| 5'-TTT CTA GAA TCA GTG GCA CTC GTT CCA CAT G-3' |
| 4) 3' M DEN-2 |
| 5'-T TTC TAG AAA GCC TGG ATG TCT CAA GAT CCA-3' |
| 5) 5' M DEN-4 |
| 5'-TTT CTA GAT TCA GTA GCT TTA ACA CCA C-3' |
| 6) 3' M DEN-4 |
| 5'-T TGA ATT CGC GAA TCT TGG GTT TCT GAG-3' |

Example 3

Coupling of Peptides to a Carrier Protein and Immunization Scheme 3.1 Coupling of Peptides to BSA The coupling of peptides was performed as follows:

1. Activation of BSA: Drop by drop and with shaking, 80 ml of the bifunctional reagent m-maleimidobenzoyl-N-hydroxysuccinimide ester (MBS) 5 m g/ml in dimethylformamide, were added to a dissolution of 2.8 mg of bovine albumin fraction V (BSA) in 250 ml of PBS. Then, it was kept in agitation at room temperature during 30 minutes, and the mixture was passed through a PD10 column.
2. Coupling of the peptide to the activated BSA: a dissolution of 1 mg of peptide dissolved in 300 ml of PBS was added to the activated BSA solution drop by drop and with shaking. It was kept at room temperature during 3 hours, and concentration was determined by the Lowry method.

3.2 Immunization Scheme

The immunization scheme of peptides linked to BSA is the following:

FIG. 5 shows the proliferative response to Dengue 2 virus antigens of spoeen T cell from peptide-immunized mice.

Male Balb/c mice of 4–6 weeks old were immunized with 50 mg of the peptide-BSA conjugate intraperitoneally. In addition, two immunization schemes were performed, one with BSA and the other with PBS. A total of 4 inoculations were carried out, each of them 15 days apart. The Freund's Complete Adjuvant was used in the first doses, and the Freund's Incomplete Adjuvant in the others. A blood sample was extracted from the retro-orbital vein seven days after the last inoculation.

The obtained sera of each scheme were placed at −20 C. to be used later.

Example 4

In vitro Plaque-reduction Neutralization Test

Neutralization technique was carried out according to Morens (Morens, D. M. et al. 1985. Simplified plaque reduction neutralization assay for dengue viruses by semimicro methods in BHK-21 cells: Comparison of the BHK suspension test with standard plaque reduction neutralization. J. Clin. Microbiol. 22 p.250).

Dilutions of anti-peptide sera and of anti-BSA controls and negative sera from 1/10 to 1/640 were prepared. Each dilution of sera was put into contact with a dilution of the virus (strain A 15 of Dengue 2) having 15–20 PFU/50 ml.

The mixture was incubated at 37 C. during 1 hour. A total of 50 ml of each mixture were added in triplicate to BHK-21 cells in plates of 24 wells, and they were incubated in a CO2 incubator at 37 C. during 4 hours. Then, 0.5 ml of carboxymethylcellulose-containing medium were added, and it was incubated again for several days considering the viral serotype used. After these days tinction and the count of lysis plaques produced by the virus were carried out.

Titer was expressed in each case as the dilution at which it was obtained the 50% of plaque number reduction.

The results are shown in Table 3.

TABLE 3

PRNT of the anti-peptide sera against 19-6 and 20-3.
Anti-peptide neutralization titer for each serotype

|  | D1 | D2 | D3 | D4 |
| --- | --- | --- | --- | --- |
| B 19-6 | 1/100 | 1/180 | 1/60 | 1/160 |
| B 20-3 | 1/110 | 1/80 | 1/80 | 1/80 |

Example 5
Identification of T Cell Epitopes

The presence of T cell epitopes in the peptides of pre-M was evaluated throughout the study of anti-peptide antibody response elicited in free peptides (non-conjugated) immunized mice. Primed animals demonstrated higher serum antibody production in response to a booster dose of antigen when compared to the response in naive animals. These results confirm the existence of B cell epitopes in these peptides and show that these sequences contains T cell epitopes, which are able to stimulate Th activity in vivo to improve the titers of antibody response.

Virus-specific proliferative responses of spleen T lymphocytes were demonstrated in peptide immunized BALB/c mice. T cells from 19-6 and 19-5 immunized mice proliferated in an in vitro blastogenesis assay when they were cultured with the dengue 2 virus. However, the 20-2 peptide did not elicit a significant proliferative response against the virus. It could contain a T cell cryptic epitope, being recognized in the free form of peptide but not like a result of the immunodominant epitopes presentation and processing of the virus in a natural infection.

Example 6
Protection Assay

Figure 6:
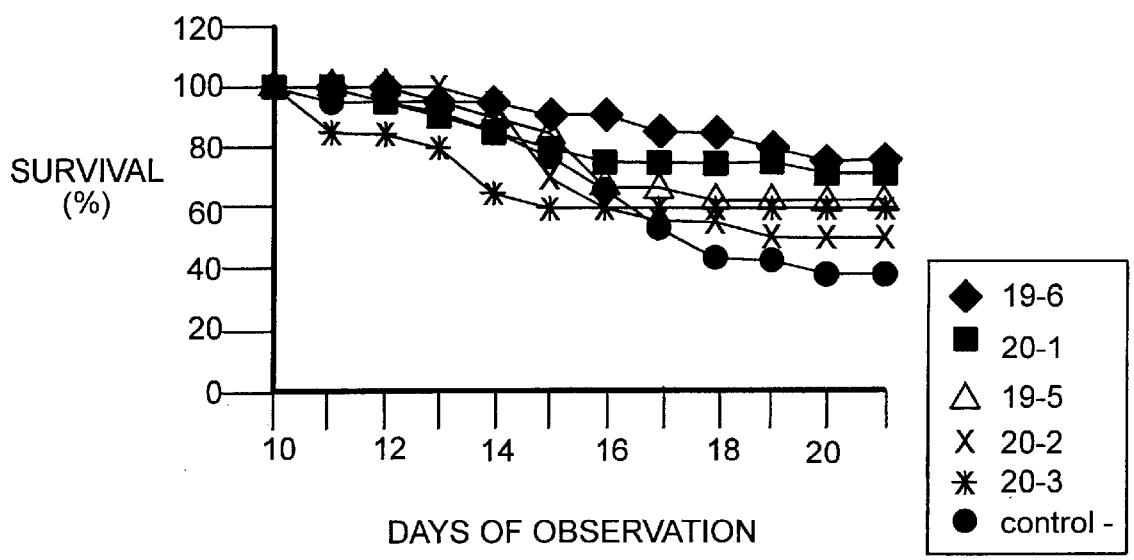
Figure 7:
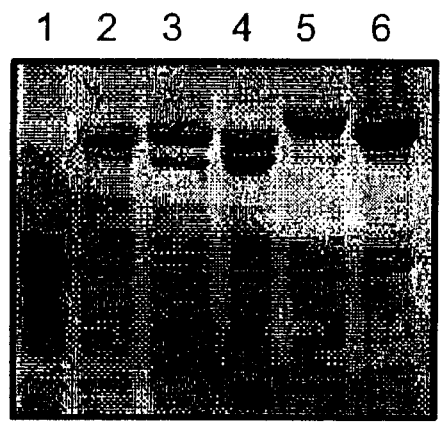
Figure 8:
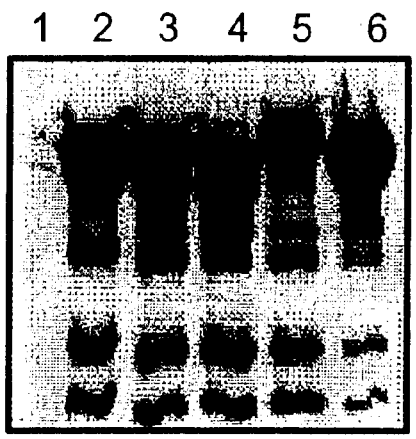

Mice were challenged 7 days after the last immunization by intracraneal injection with an dilution of 1/2500 (corresponding to 100 LD50 lethal doses) of live, mouse-adapted dengue-2 virus (strain A15). Mice were observed for up to 21 days for morbidity and mortality. Data were tested for statistical significance using Fisher's test. The percent survival in peptide immunized and control animals are shown in FIG. 6. The level of protection induced for the peptides 19-5, 19-6 and 20-1 was statistically significant (p<0,05).

Example 7
Indirect ELISA to Detect Anti-peptide Antibodies
Human Sera

Peptides 19-6, 20-1, 20-2, 20-3 were fixed to the plates in a 10 m g/ml concentration in coating buff they were incubated at 4 C. overnight Sera were added diluted 1/200 in PBS-Tween 20. Finally, total human /peroxidase anti-immunoglobuline conjugate was added, and subsequently, the substrate (orthophenylendiamine, H2O2, 0.05 M phosphate citrate buffer, pH 5) was added. The reading was carried out in an ELISA reader at 492 nm and the cut-off value for each peptide was determined.

The sera used were from subjects having viral clinical infection that was serologically diagnosed as Dengue by the techniques of Inhibition of the hemagglutination (Clarke, D. H. y Casals, J. 1958. Techniques for hemagglutination and hemagglutination—inhibition with Arthropod Borne Virus. Am. J. Trop. Med. Hyg. 7 p.561) and ELISA of inhibition (Vzquez, S., Fernndez, R. 1989. Utilizacin de un mtodo de ELISA de Inhibicin en el diagnstico serolgico de dengue. Rev. Cub. Med. Trop. 41(1) p18-26) for total anti-dengue antibodies.

The study induded 118 sera from patents of the epidemics occurred in Cuba 1981, Panama 1994 and Costa Rica 1994. Dengue virus 2 was isolated in these epidemics, besides serotype 1 and 4 in Costa Rica; they were classified according to the titers of inhibiting antibodies of hemagglutination in cases of primary and secondary infections.

The 46.6% of the sera were positive to the 4 peptides used. Percentages of positivity of 56.8%, 79.6%, 77.1% and 83.1% to peptides B 19-6, 20-1, 20-2, and 20-3 were obtained respectively.

The average of the reactivity index, calculated by the optical density quotient of the sample/cut-off value, for each peptide was 1.07, 1.52, 1.57 and 1.49 for each peptide.
Mouse Sera The indirect ELISA used was as described above but using an anti-mouse Ig conjugated to peroxidase. Antibody titers obtained in the anti-peptides sera were generally above 1/10 000.

Example 8
Insertion of Pre-M/M Fragments in the P64k Protein of *Neisseria meningitidis*

In this example we expressed fragments of the pre-M/M protein of Dengue 2 (A 15 strain) and of Dengue 4 (814669 strain) (Zhao, B. et al. 1986. Cloning full-length dengue type 4 viral DNA sequences: analysis of genes coding for structural proteins. Virol. 155 p.77) inserted in a *N. meningitidis* protein previously characterized in our group (Silva, R. et al. 1992. Nucleotide sequence coding for an outer membrane protein from *Neisseria meningitidis* and use of said protein in vaccine preparations. European Patent 0 474 313, 1997): P64k, which have demonstrated to be highly immunogenic in several animal models. Besides, the level of expression of P64k in *E. coli* reaches more than 30% of the total protein of the bacteria.

P64k protein (64 kDa) of dimeric nature, has two functional domains in each subunit: one with lipoic acid-binding activity (1–100) and the other with lipoamide-dehydrogenase activity (117–594). Both have been identified as conformational domains relatively independent by crystallography of X-rays (Li de la Sierra, 1. et al. 1994. Crystallization and preliminary X-ray investigation of a recombinant outer membrane protein from *Neisseria meningitidis*. J. Mol. Biol. 235 p.1154; Li de la Sierra, I. et al. 1997. Molecular structure of the lypoamide dehydrogenase domain of a surface antigen from *Neisseria meningitidis*. J. Mol. Biol. 269 p.129).

The former was selected (in the aminoacidic position 45) to perform the insertions of fragments 1–42 and 92–133 of pre-M/M, because this little domain is more exposed and does not seem to be involved in dimer-formation. This suggested that the global structure of the chimeric protein with respect to the natural P64k would be less altered than if an insertion site were made in the domain 117–594, which, in addition participates directly in the formation of the dimer.

The region coding for amino acids 44–53 (TLETDKATMD), which include the region of lipoic acid binding of the P64k gene used in the production of fusion proteins, was preliminary changed to TLDLEMD. This modification was carried out to avoid the recognition of P64k by the sera of patients having primary cirrhosis, who have self-antibodies against homologous epitopes present in the human dehydrolipoamide acetyltransferase mytochondrial (Tuaillon, N. et al. 1992. A lipoyl synthetic octadecapeptide of dihydrolipoamide acetyl transferase specifically recognized by anti-M2 autoantibodies in primary biliary cirrhosis. J. Immunol. 148 p.445).

The strategy to produce the two clones is explained below:

Fragments Pre-2, M-2 and M-4 were amplified by Polymerase Chain Reaction, using the combination of oligonucleotides 1 and 2, 3 and 4, and 5 and 6, respectively (see Table 2), and using pD-5 plasmid as template. This pD-5 plasmid includes a copy of preM/M gene from Dengue-2 virus (strain A-15) cloned into pBluescript vector (stratagene). DNA bands obtained in each case (120 bp) were digested with Xba I (Pre-2 and M-2) or Xba I/EcoR I (M-4), and they were cloned into the corresponding sites that were artificially created in position 135–145 of P64k gene, cloned into vector pM-92. Besides, a chimeric clone that include M-2 and M-4 bands in the already mentioned sites Xba I and EcoR I was generated by triple ligation. Recombinant clones bearing the inserts in the right orientation were identified by restriction analysis and DNA-sequencing.

The fusion proteins generated by clones of Pre-2 (pD31) SEQ ID NO.:6, M-2 (pD30) SEQ ID NO.:7, M-2/M-4 (pD33) SEQ ID NO.:9, and M-4 (pD34) SEQ ID NO.:8 were expressed under the promoter of the tryptophan operon (ptrp) in the *E. coli* strain MM294 (F-end A1 hsdR17 (rk– mk+) sup E44 thi-1 relA1? RfbD1? SpoT1?). All were obtained in the expected sizes and with levels of expression up to 30% of the total proteins of the bacteria, though PD31 protein showed a high instability (FIG. 7). All fusion proteins were recognized by some mouse monoclonal antibodies anti-P64k in ELISA (data not shown) and Western blotting (FIG. 8), where a remarkable degradation in the whole-cell extract was detected. The amino acid sequence of these proteins is shown the Sequence List.

Mouse immunization with PD33 and PD34 fusion proteins semipurified by a non-denaturalizing protocol, has elicited high titers against them in ELISA (up to 1/100 000), and at the same time antibodies with titers up to 1/4000 in ELISA against the synthetic peptides have been obtained.

BREIF DESCRIPTION OF THE FIGURES

FIGS. 1A–1B. Hydrophylicity, accessibility and flexibility profiles of pre-(A) and M (B) proteins of Dengue virus.

FIGS. 2A–2B. Prediction of the secondary structure and of accessibility of pre (A) and M (protein). AA: amino acids. PHD sec: prediction of secondary structure (E=beta, H=helix, L=loop) P-3 acc. Prediction of accessibility (e=exposed, b=non-exposed). Sub sec (Sub acc) residues in which the prediction of secondary structure (accessibility) is 82.4% (70%) efficacious.

FIG. 3. Variability profiles of pre- and M proteins. Variability was calculated considering 3 sets of Flavivirus sequences. Dengue: sequences of 15 Dengue isolations. MBV: Flavivirus sequences transmitted by mosquitoes that include Dengue virus, Kunji, West Nile Virus, Murray Valley Encephalitis and Saint Louis Encephalitis. Flavivirus: sequences of more than 30 different flaviviral isolations: (MBV+Yellow fever, Langat, Louping III and Tick-Borne Encephalitis).

FIGS. 4A–4B. Prediction of T cell epitopes of pre (A) and M (B) proteins: AMPHI 7 (11): prediction of amphipatic segments of 7 (11) residues, positive residues are the central amino acids of an amphipatic block potentially antigenic. RT 4 (5): prediction of antigenic profiles of 4 (5) residues, positive residues are those who fulfill the profiles.

FIG. 5. Proliferative response to dengue 2 virus antigens (at concentrations of 10, 20 and 40 m g/ml) of spleen T cells from peptides-immunized mice 19-6, 19-5 and 20-2.

FIG. 6. Percent survival in peptide immunized and control animals. The level of protection induced for the peptides 19-5, 19-6 and 20-1 was statistically significant.

FIG. 7. 10% SDS-PAGE of MM294 *E. coli* strain transformed with fusion proteins and P64k protein (pM-92 plasmid). Lanes: 1-Untransformed MM294 strain, 2-pM-92/MM294, 3-pD-30/MM294, 4-pD-31/MM294, 5-pD-33/MM294, 6-pD-34/MM294.

FIG. 8. Western blot using AcM 114 of MM294 *E. coli* strain transformed with fusion proteins and P64k protein (pM-92 plasmid). Lanes: 1-Untransformed MM294 strain, 2-pM-92/MM294, 3-pD-30/MM294, 4-pD-31/MM294, 5-pD-33/MM294, 6-pD-34/MM294.

What is claimed is:

1. An isolated peptide or mimetic compound comprising a sequence of no more than about 40 amino acids from Dengue virus preM/M, wherein the sequence of amino acids from Dengue virus preM/M comprises an epitope found within a sequence selected from the group consisting of SEQ ID No.: 1, SEQ ID No.: 2, SEQ ID No.: 3, SEQ ID No.: 4 and SEQ ID No.: 5.

2. The isolated peptide according to claim 1, wherein the amino acid sequence of Dengue virus pre-M/M is of a first serotype; and wherein the amino acid sequence of Dengue virus pre-M/M of the first serotype includes an epitope that is cross-reactive with Dengue virus pre-M/M of a second serotype.

3. The isolated peptide or mimetic compound according to claim 2, wherein the amino acid sequence of Dengue virus pre-M/M is cross-reactive with Dengue virus pre-M/M of more than one serotype.

4. The isolated peptide or mimetic compound according to claim 1, wherein the peptide or mimetic compound elicits a proliferative response of spleen T lymphocytes against Dengue 2 virus.

5. The isolated peptide or mimetic compound according to claim 1, wherein the peptide or mimetic compound elicits an antibody in a mammal.

6. The isolated peptide or mimetic compound according to claim 5, wherein the antibody elicited is protective against Dengue virus infection.

* * * * *

UNITED STATES PATENT AND TRADEMARK OFFICE
CERTIFICATE OF CORRECTION

PATENT NO.    : 6,383,488 B1
DATED         : July 16, 2002
INVENTOR(S)   : Ramudo et al.

It is certified that error appears in the above-identified patent and that said Letters Patent is hereby corrected as shown below:

<u>Column 1,</u>
Line 61, now reads "Adidotropic amines", should read -- Acidotropic amines --;

<u>Column 2,</u>
Line 53, now reads "altematively, to include", should read -- alternatively, to include --;

<u>Column 3,</u>
Line 58, now reads "amino acids 3-11", should read -- amino acids 3-31 --;

<u>Column 4,</u>
Line 11, now reads "Dengue virus scrotypes", should read -- Dengue virus serotypes --;

<u>Column 5,</u>
Line 1, now reads "Predictions of humoral amino acid", should read -- Predictions of humoral antigenicity --;
Line 14, now reads "Hoop, T.P. y Woods, K.R. 1981." should read -- Hopp, T.P. and Woods, K.R. 1981. --;

<u>Column 6,</u>
Line 27, now reads "at least 5 add residues", should read -- at least 5 acid residues --;
Line 27, now reads "the region 4045", should read -- the region 40-65 --;

<u>Column 7,</u>
Line 31, now reads "Asn, Gin", should read -- Asn, Gln --;

<u>Column 9,</u>
Line 66, now reads "in coating buff", should read -- in coating buffer, then --;

<u>Column 10,</u>
Line 17, now reads "the study induded", should read -- the study included --;
Line 17, now reads "sera from patents", should read -- sera from patients --;

UNITED STATES PATENT AND TRADEMARK OFFICE
CERTIFICATE OF CORRECTION

PATENT NO. : 6,383,488 B1
DATED : July

SEQUENCE LISTING

```
<160> NUMBER OF SEQ ID NOS:  9

<210> SEQ ID NO 1
<211> LENGTH: 29
<212> TYPE: PRT
<213> ORGANISM: Dengue virus

<400> SEQUENCE: 1

Leu Thr Thr Arg Asn Gly Glu Pro His Met Ile Val Met Arg Gln Glu
  1               5                  10                  15

Lys Gly Lys Ser Leu Leu Phe Lys Thr Gly Asp Gly Val
             20                  25
```

-continued

```
<210> SEQ ID NO 2
<211> LENGTH: 23
<212> TYPE: PRT
<213> ORGANISM: Dengue virus

<400> SEQUENCE: 2

Cys Glu Asp Thr Ile Thr Tyr Lys Cys Pro Leu Leu Arg Gln Asn Glu
 1               5                  10                  15

Pro Glu Asp Ile Asp Cys Trp
            20

<210> SEQ ID NO 3
<211> LENGTH: 36
<212> TYPE: PRT
<213> ORGANISM: Dengue virus

<400> SEQUENCE: 3

Arg Gln Asn Glu Pro Glu Asp Ile Asp Cys Trp Cys Asn Ser Thr Ser
 1               5                  10                  15

Thr Trp Val Thr Tyr Gly Thr Cys Thr Thr Thr Gly Glu His Arg Arg
            20                  25                  30

Glu Lys Arg Ser
        35

<210> SEQ ID NO 4
<211> LENGTH: 25
<212> TYPE: PRT
<213> ORGANISM: Dengue virus

<400> SEQUENCE: 4

Asn Ser Thr Ser Thr Trp Val Thr Tyr Gly Thr Cys Thr Thr Thr Gly
 1               5                  10                  15

Glu His Arg Arg Glu Lys Arg Ser Val
            20                  25

<210> SEQ ID NO 5
<211> LENGTH: 22
<212> TYPE: PRT
<213> ORGANISM: Dengue virus

<400> SEQUENCE: 5

Leu Glu Thr Arg Thr Glu Thr Trp Met Ser Ser Glu Gly Ala Trp Lys
 1               5                  10                  15

His Ala Gln Arg Ile Glu
            20

<210> SEQ ID NO 6
<211> LENGTH: 635
<212> TYPE: PRT
<213> ORGANISM: Artificial Sequence
<220> FEATURE:
<223> OTHER INFORMATION: Description of Artificial Sequence: Fusion
      Protein of Dengue virus preM/M and Neisseria meningitidis
      P64k protein.

<400> SEQUENCE: 6

Met Ala Leu Val Glu Leu Lys Val Pro Asp Ile Gly Gly His Glu Asn
 1               5                  10                  15

Val Asp Ile Ile Ala Val Glu Val Asn Val Gly Asp Thr Ile Ala Val
            20                  25                  30

Asp Asp Thr Leu Ile Thr Leu Asp Leu Asp Phe His Leu Thr Thr Arg
```

-continued

```
                35                  40                  45
    Asn Gly Glu Pro His Met Ile Val Ser Arg Gln Glu Lys Gly Lys Ser
                    50                  55                  60

Leu Leu Phe Lys Thr Gly Asp Gly Val Asn Met Cys Thr Leu Met Ala
    65                  70                  75                  80

Met Asp Leu Gly Leu Glu Met Asp Val Pro Ala Glu Val Ala Gly Val
                        85                  90                  95

Val Lys Glu Val Lys Val Lys Val Gly Asp Lys Ile Ser Glu Gly Gly
                    100                 105                 110

Leu Ile Val Val Val Glu Ala Glu Gly Thr Ala Ala Pro Lys Ala
                115                 120                 125

Glu Ala Ala Ala Pro Ala Gln Glu Ala Pro Lys Ala Ala Ala Pro
    130                 135                 140

Ala Pro Gln Ala Ala Gln Phe Gly Gly Ser Ala Asp Ala Glu Tyr Asp
    145                 150                 155                 160

Val Val Val Leu Gly Gly Gly Pro Gly Gly Tyr Ser Ala Ala Phe Ala
                    165                 170                 175

Ala Ala Asp Glu Gly Leu Lys Val Ala Ile Val Glu Arg Tyr Lys Thr
                180                 185                 190

Leu Gly Gly Val Cys Leu Asn Val Gly Cys Ile Pro Ser Lys Ala Leu
                195                 200                 205

Leu His Asn Ala Ala Val Ile Asp Glu Val Arg His Leu Ala Ala Asn
                210                 215                 220

Gly Ile Lys Tyr Pro Glu Pro Glu Leu Asp Ile Asp Met Leu Arg Ala
    225                 230                 235                 240

Tyr Lys Asp Gly Val Val Ser Arg Leu Thr Gly Gly Leu Ala Gly Met
                    245                 250                 255

Ala Lys Ser Arg Lys Val Asp Val Ile Gln Gly Asp Gly Gln Phe Leu
                260                 265                 270

Asp Pro His His Leu Glu Val Ser Leu Thr Ala Gly Asp Ala Tyr Glu
                275                 280                 285

Gln Ala Ala Pro Thr Gly Glu Lys Lys Ile Val Ala Phe Lys Asn Cys
    290                 295                 300

Ile Ile Ala Ala Gly Ser Arg Val Thr Lys Leu Pro Phe Ile Pro Glu
    305                 310                 315                 320

Asp Pro Arg Ile Ile Asp Ser Ser Gly Ala Leu Ala Leu Lys Glu Val
                    325                 330                 335

Pro Gly Lys Leu Leu Ile Ile Gly Gly Ile Ile Gly Leu Glu Met
                340                 345                 350

Gly Thr Val Tyr Ser Thr Leu Gly Ser Arg Leu Asp Val Val Glu Met
                355                 360                 365

Met Asp Gly Leu Met Gln Gly Ala Asp Arg Asp Leu Val Lys Val Trp
    370                 375                 380

Gln Lys Gln Asn Glu Tyr Arg Phe Asp Asn Ile Met Val Asn Thr Lys
    385                 390                 395                 400

Thr Val Ala Val Glu Pro Lys Glu Asp Gly Val Tyr Val Thr Phe Glu
                    405                 410                 415

Gly Ala Asn Ala Pro Lys Glu Pro Gln Arg Tyr Asp Ala Val Leu Val
                420                 425                 430

Ala Ala Gly Arg Ala Pro Asn Gly Lys Leu Ile Ser Ala Glu Lys Ala
                435                 440                 445

Gly Val Ala Thr Asp Arg Gly Phe Ile Glu Val Asp Lys Gln Met
                450                 455                 460
```

```
Arg Thr Asn Val Pro His Ile Tyr Ala Ile Gly Asp Ile Val Gly Gln
465                 470                 475                 480

Pro Met Leu Ala His Lys Ala Val His Glu Gly His Val Ala Ala Glu
            485                 490                 495

Asn Cys Ala Gly His Lys Ala Tyr Phe Asp Ala Arg Val Ile Pro Gly
            500                 505                 510

Val Ala Tyr Thr Ser Pro Glu Val Ala Trp Val Gly Glu Thr Glu Leu
            515                 520                 525

Ser Ala Lys Ala Ser Gly Arg Lys Ile Thr Lys Ala Asn Phe Pro Trp
530                 535                 540

Ala Ala Ser Gly Arg Ala Ile Ala Asn Gly Cys Asp Lys Pro Phe Thr
545                 550                 555                 560

Lys Leu Ile Phe Asp Ala Glu Thr Gly Arg Ile Ile Gly Gly Gly Ile
            565                 570                 575

Val Gly Pro Asn Gly Gly Asp Met Ile Gly Glu Val Cys Leu Ala Ile
            580                 585                 590

Glu Met Gly Cys Asp Ala Ala Asp Ile Gly Lys Thr Ile His Pro His
            595                 600                 605

Pro Thr Leu Gly Glu Ser Ile Gly Met Ala Ala Glu Val Ala Leu Gly
            610                 615                 620

Thr Cys Thr Asp Leu Pro Pro Gln Lys Lys Lys
625                 630                 635

<210> SEQ ID NO 7
<211> LENGTH: 635
<212> TYPE: PRT
<213> ORGANISM: Artificial Sequence
<220> FEATURE:
<223> OTHER INFORMATION: Description of Artificial Sequence: Fusion
      Protein of Dengue virus preM/M and Neisseria meningitidis
      P64k protein.

<400> SEQUENCE: 7

Met Ala Leu Val Glu Leu Lys Val Pro Asp Ile Gly Gly His Glu Asn
1               5                   10                  15

Val Asp Ile Ile Ala Val Glu Val Asn Val Gly Asp Thr Ile Ala Val
                20                  25                  30

Asp Asp Thr Leu Ile Thr Leu Asp Leu Glu Ser Val Ala Leu Val Pro
            35                  40                  45

His Val Gly Met Gly Leu Glu Thr Arg Thr Glu Thr Trp Met Ser Ser
        50                  55                  60

Glu Gly Ala Trp Lys His Ala Gln Arg Ile Glu Thr Trp Ile Leu Arg
65                  70                  75                  80

His Pro Gly Phe Leu Glu Met Asp Val Pro Ala Glu Val Ala Gly Val
                85                  90                  95

Val Lys Glu Val Lys Val Lys Val Gly Asp Lys Ile Ser Glu Gly Gly
                100                 105                 110

Leu Ile Val Val Glu Ala Glu Gly Thr Ala Ala Pro Lys Ala
            115                 120                 125

Glu Ala Ala Ala Pro Ala Gln Glu Ala Pro Lys Ala Ala Ala Pro
130                 135                 140

Ala Pro Gln Ala Ala Gln Phe Gly Gly Ser Ala Asp Ala Glu Tyr Asp
145                 150                 155                 160

Val Val Val Leu Gly Gly Pro Gly Gly Tyr Ser Ala Ala Phe Ala
                165                 170                 175
```

-continued

```
Ala Ala Asp Glu Gly Leu Lys Val Ala Ile Val Glu Arg Tyr Lys Thr
            180                 185                 190

Leu Gly Gly Val Cys Leu Asn Val Gly Cys Ile Pro Ser Lys Ala Leu
            195                 200                 205

Leu His Asn Ala Ala Val Ile Asp Glu Val Arg His Leu Ala Ala Asn
            210                 215                 220

Gly Ile Lys Tyr Pro Glu Pro Glu Leu Asp Ile Asp Met Leu Arg Ala
225                 230                 235                 240

Tyr Lys Asp Gly Val Val Ser Arg Leu Thr Gly Gly Leu Ala Gly Met
                245                 250                 255

Ala Lys Ser Arg Lys Val Asp Val Ile Gln Gly Asp Gly Gln Phe Leu
            260                 265                 270

Asp Pro His His Leu Glu Val Ser Leu Thr Ala Gly Asp Ala Tyr Glu
            275                 280                 285

Gln Ala Ala Pro Thr Gly Glu Lys Lys Ile Val Ala Phe Lys Asn Cys
            290                 295                 300

Ile Ile Ala Ala Gly Ser Arg Val Thr Lys Leu Pro Phe Ile Pro Glu
305                 310                 315                 320

Asp Pro Arg Ile Ile Asp Ser Ser Gly Ala Leu Ala Leu Lys Glu Val
                325                 330                 335

Pro Gly Lys Leu Leu Ile Ile Gly Gly Gly Ile Ile Gly Leu Glu Met
            340                 345                 350

Gly Thr Val Tyr Ser Thr Leu Gly Ser Arg Leu Asp Val Val Glu Met
            355                 360                 365

Met Asp Gly Leu Met Gln Gly Ala Asp Arg Asp Leu Val Lys Val Trp
            370                 375                 380

Gln Lys Gln Asn Glu Tyr Arg Phe Asp Asn Ile Met Val Asn Thr Lys
385                 390                 395                 400

Thr Val Ala Val Glu Pro Lys Glu Asp Gly Val Tyr Val Thr Phe Glu
                405                 410                 415

Gly Ala Asn Ala Pro Lys Glu Pro Gln Arg Tyr Asp Ala Val Leu Val
            420                 425                 430

Ala Ala Gly Arg Ala Pro Asn Gly Lys Leu Ile Ser Ala Glu Lys Ala
            435                 440                 445

Gly Val Ala Val Thr Asp Arg Gly Phe Ile Glu Val Asp Lys Gln Met
            450                 455                 460

Arg Thr Asn Val Pro His Ile Tyr Ala Ile Gly Asp Ile Val Gly Gln
465                 470                 475                 480

Pro Met Leu Ala His Lys Ala Val His Glu Gly His Val Ala Ala Glu
                485                 490                 495

Asn Cys Ala Gly His Lys Ala Tyr Phe Asp Ala Arg Val Ile Pro Gly
            500                 505                 510

Val Ala Tyr Thr Ser Pro Glu Val Ala Trp Val Gly Glu Thr Glu Leu
            515                 520                 525

Ser Ala Lys Ala Ser Gly Arg Lys Ile Thr Lys Ala Asn Phe Pro Trp
            530                 535                 540

Ala Ala Ser Gly Arg Ala Ile Ala Asn Gly Cys Asp Lys Pro Phe Thr
545                 550                 555                 560

Lys Leu Ile Phe Asp Ala Glu Thr Gly Arg Ile Ile Gly Gly Gly Ile
                565                 570                 575

Val Gly Pro Asn Gly Gly Asp Met Ile Gly Glu Val Cys Leu Ala Ile
            580                 585                 590

Glu Met Gly Cys Asp Ala Ala Asp Ile Gly Lys Thr Ile His Pro His
```

```
              595                 600                 605
Pro Thr Leu Gly Glu Ser Ile Gly Met Ala Ala Glu Val Ala Leu Gly
            610                 615                 620

Thr Cys Thr Asp Leu Pro Pro Gln Lys Lys Lys
625                 630                 635

<210> SEQ ID NO 8
<211> LENGTH: 677
<212> TYPE: PRT
<213> ORGANISM: Artificial Sequence
<220> FEATURE:
<223> OTHER INFORMATION: Description of Artificial Sequence: Fusion
      Protein of Dengue virus preM/M and Neisseria meningitidis
      P64k protein.

<400> SEQUENCE: 8

Met Ala Leu Val Glu Leu Lys Val Pro Asp Ile Gly Gly His Glu Asn
  1               5                  10                  15

Val Asp Ile Ile Ala Val Glu Val Asn Val Gly Asp Thr Ile Ala Val
                 20                  25                  30

Asp Asp Thr Leu Ile Thr Leu Asp Leu Asp Phe His Leu Thr Thr Arg
             35                  40                  45

Asn Gly Glu Pro His Met Ile Val Ser Arg Gln Glu Lys Gly Lys Ser
         50                  55                  60

Leu Leu Phe Lys Thr Gly Asp Gly Val Asn Met Cys Thr Leu Met Ala
 65                  70                  75                  80

Met Asp Leu Gly Ser Val Ala Leu Val Pro His Val Gly Met Gly Leu
                 85                  90                  95

Glu Thr Arg Thr Glu Thr Trp Met Ser Ser Gly Ala Trp Lys His
            100                 105                 110

Ala Gln Arg Ile Glu Thr Trp Ile Leu Arg His Pro Gly Phe Leu Glu
            115                 120                 125

Met Asp Val Pro Ala Glu Val Ala Gly Val Val Lys Glu Val Lys Val
        130                 135                 140

Lys Val Gly Asp Lys Ile Ser Glu Gly Gly Leu Ile Val Val Val Glu
145                 150                 155                 160

Ala Glu Gly Thr Ala Ala Pro Lys Ala Glu Ala Ala Ala Pro
                165                 170                 175

Ala Gln Glu Ala Pro Lys Ala Ala Pro Ala Pro Gln Ala Ala Gln
            180                 185                 190

Phe Gly Gly Ser Ala Asp Ala Glu Tyr Asp Val Val Leu Gly Gly
            195                 200                 205

Gly Pro Gly Gly Tyr Ser Ala Ala Phe Ala Ala Ala Asp Glu Gly Leu
        210                 215                 220

Lys Val Ala Ile Val Glu Arg Tyr Lys Thr Leu Gly Gly Val Cys Leu
225                 230                 235                 240

Asn Val Gly Cys Ile Pro Ser Lys Ala Leu Leu His Asn Ala Ala Val
                245                 250                 255

Ile Asp Glu Val Arg His Leu Ala Ala Asn Gly Ile Lys Tyr Pro Glu
            260                 265                 270

Pro Glu Leu Asp Ile Asp Met Leu Arg Ala Tyr Lys Asp Gly Val Val
        275                 280                 285

Ser Arg Leu Thr Gly Gly Leu Ala Gly Met Ala Lys Ser Arg Lys Val
    290                 295                 300

Asp Val Ile Gln Gly Asp Gly Gln Phe Leu Asp Pro His His Leu Glu
305                 310                 315                 320
```

Val Ser Leu Thr Ala Gly Asp Ala Tyr Glu Gln Ala Pro Thr Gly
            325                 330                 335

Glu Lys Lys Ile Val Ala Phe Lys Asn Cys Ile Ile Ala Ala Gly Ser
            340                 345                 350

Arg Val Thr Lys Leu Pro Phe Ile Pro Glu Asp Pro Arg Ile Ile Asp
            355                 360                 365

Ser Ser Gly Ala Leu Ala Leu Lys Glu Val Pro Gly Lys Leu Leu Ile
    370                 375                 380

Ile Gly Gly Gly Ile Ile Gly Leu Glu Met Gly Thr Val Tyr Ser Thr
385                 390                 395                 400

Leu Gly Ser Arg Leu Asp Val Val Glu Met Met Asp Gly Leu Met Gln
            405                 410                 415

Gly Ala Asp Arg Asp Leu Val Lys Val Trp Gln Lys Gln Asn Glu Tyr
            420                 425                 430

Arg Phe Asp Asn Ile Met Val Asn Thr Lys Thr Val Ala Val Glu Pro
            435                 440                 445

Lys Glu Asp Gly Val Tyr Val Thr Phe Glu Gly Ala Asn Ala Pro Lys
    450                 455                 460

Glu Pro Gln Arg Tyr Asp Ala Val Leu Val Ala Ala Gly Arg Ala Pro
465                 470                 475                 480

Asn Gly Lys Leu Ile Ser Ala Glu Lys Ala Gly Val Ala Val Thr Asp
            485                 490                 495

Arg Gly Phe Ile Glu Val Asp Lys Gln Met Arg Thr Asn Val Pro His
            500                 505                 510

Ile Tyr Ala Ile Gly Asp Ile Val Gly Gln Pro Met Leu Ala His Lys
            515                 520                 525

Ala Val His Glu Gly His Val Ala Ala Glu Asn Cys Ala Gly His Lys
    530                 535                 540

Ala Tyr Phe Asp Ala Arg Val Ile Pro Gly Val Ala Tyr Thr Ser Pro
545                 550                 555                 560

Glu Val Ala Trp Val Gly Glu Thr Glu Leu Ser Ala Lys Ala Ser Gly
            565                 570                 575

Arg Lys Ile Thr Lys Ala Asn Phe Pro Trp Ala Ala Ser Gly Arg Ala
            580                 585                 590

Ile Ala Asn Gly Cys Asp Lys Pro Phe Thr Lys Leu Ile Phe Asp Ala
    595                 600                 605

Glu Thr Gly Arg Ile Ile Gly Gly Gly Ile Val Gly Pro Asn Gly Gly
            610                 615                 620

Asp Met Ile Gly Glu Val Cys Leu Ala Ile Glu Met Gly Cys Asp Ala
625                 630                 635                 640

Ala Asp Ile Gly Lys Thr Ile His Pro His Pro Thr Leu Gly Glu Ser
            645                 650                 655

Ile Gly Met Ala Ala Glu Val Ala Leu Gly Thr Cys Thr Asp Leu Pro
            660                 665                 670

Pro Gln Lys Lys Lys
        675

<210> SEQ ID NO 9
<211> LENGTH: 635
<212> TYPE: PRT
<213> ORGANISM: Artificial Sequence
<220> FEATURE:
<223> OTHER INFORMATION: Description of Artificial Sequence: Fusion
      Protein of Dengue virus preM/M and Neisseria meningitidis
      P64k protein.

<400> SEQUENCE: 9

| | | | | | | | | | | | | | | |
|---|---|---|---|---|---|---|---|---|---|---|---|---|---|---|
|Met|Ala|Leu|Val|Glu|Leu|Lys|Val|Pro|Asp|Ile|Gly|Gly|His|Glu|Asn|
|1| | | |5| | | |10| | | |15| | |

Val Asp Ile Ile Ala Val Glu Val Asn Val Gly Asp Thr Ile Ala Val
                 20                 25                 30

Asp Asp Thr Leu Ile Thr Leu Asp Leu Glu Ser Val Ala Leu Thr Pro
        35                 40                 45

His Ser Gly Met Gly Leu Glu Thr Arg Ala Glu Thr Trp Met Ser Ser
  50               55                 60

Glu Gly Ala Trp Lys His Ala Gln Arg Val Glu Ser Trp Ile Leu Arg
65              70               75             80

Asn Pro Arg Phe Leu Glu Met Asp Val Pro Ala Glu Val Ala Gly Val
            85             90               95

Val Lys Glu Val Lys Val Lys Val Gly Asp Lys Ile Ser Glu Gly Gly
           100             105           110

Leu Ile Val Val Glu Ala Glu Thr Ala Ala Pro Lys Ala
    115              120           125

Glu Ala Ala Ala Pro Ala Gln Glu Ala Pro Lys Ala Ala Pro
130             135            140

Ala Pro Gln Ala Ala Gln Phe Gly Gly Ser Ala Asp Ala Glu Tyr Asp
145            150            155           160

Val Val Val Leu Gly Gly Gly Pro Gly Gly Tyr Ser Ala Ala Phe Ala
           165            170           175

Ala Ala Asp Glu Gly Leu Lys Val Ala Ile Val Glu Arg Tyr Lys Thr
           180            185           190

Leu Gly Gly Val Cys Leu Asn Val Gly Cys Ile Pro Ser Lys Ala Leu
    195              200            205

Leu His Asn Ala Ala Val Ile Asp Glu Val Arg His Leu Ala Ala Asn
    210              215           220

Gly Ile Lys Tyr Pro Glu Pro Glu Leu Asp Ile Asp Met Leu Arg Ala
225              230            235           240

Tyr Lys Asp Gly Val Val Ser Arg Leu Thr Gly Gly Leu Ala Gly Met
           245            250           255

Ala Lys Ser Arg Lys Val Asp Val Ile Gln Gly Asp Gly Gln Phe Leu
           260            265           270

Asp Pro His His Leu Glu Val Ser Leu Thr Ala Gly Asp Ala Tyr Glu
        275              280           285

Gln Ala Ala Pro Thr Gly Glu Lys Lys Ile Val Ala Phe Lys Asn Cys
    290              295           300

Ile Ile Ala Ala Gly Ser Arg Val Thr Lys Leu Pro Phe Ile Pro Glu
305              310            315           320

Asp Pro Arg Ile Ile Asp Ser Ser Gly Ala Leu Ala Leu Lys Glu Val
           325            330           335

Pro Gly Lys Leu Leu Ile Ile Gly Gly Gly Ile Ile Gly Leu Glu Met
           340            345           350

Gly Thr Val Tyr Ser Thr Leu Gly Ser Arg Leu Asp Val Val Glu Met
           355            360           365

Met Asp Gly Leu Met Gln Gly Ala Asp Arg Asp Leu Val Lys Val Trp
         370             375           380

Gln Lys Gln Asn Glu Tyr Arg Phe Asp Asn Ile Met Val Asn Thr Lys
385              390            395           400

Thr Val Ala Val Glu Pro Lys Glu Asp Gly Val Tyr Val Thr Phe Glu

-continued

```
                            405                 410                 415
Gly Ala Asn Ala Pro Lys Glu Pro Gln Arg Tyr Asp Ala Val Leu Val
                420                 425                 430

Ala Ala Gly Arg Ala Pro Asn Gly Lys Leu Ile Ser Ala Glu Lys Ala
            435                 440                 445

Gly Val Ala Val Thr Asp Arg Gly Phe Ile Glu Val Asp Lys Gln Met
        450                 455                 460

Arg Thr Asn Val Pro His Ile Tyr Ala Ile Gly Asp Ile Val Gly Gln
465                 470                 475                 480

Pro Met Leu Ala His Lys Ala Val His Glu Gly His Val Ala Ala Glu
                485                 490                 495

Asn Cys Ala Gly His Lys Ala Tyr Phe Asp Ala Arg Val Ile Pro Gly
            500                 505                 510

Val Ala Tyr Thr Ser Pro Glu Val Ala Trp Val Gly Glu Thr Glu Leu
        515                 520                 525

Ser Ala Lys Ala Ser Gly Arg Lys Ile Thr Lys Ala Asn Phe Pro Trp
    530                 535                 540

Ala Ala Ser Gly Arg Ala Ile Ala Asn Gly Cys Asp Lys Pro Phe Thr
545                 550                 555                 560

Lys Leu Ile Phe Asp Ala Glu Thr Gly Arg Ile Ile Gly Gly Gly Ile
                565                 570                 575

Val Gly Pro Asn Gly Gly Asp Met Ile Gly Glu Val Cys Leu Ala Ile
            580                 585                 590

Glu Met Gly Cys Asp Ala Ala Asp Ile Gly Lys Thr Ile His Pro His
        595                 600                 605

Pro Thr Leu Gly Glu Ser Ile Gly Met Ala Ala Glu Val Ala Leu Gly
    610                 615                 620

Thr Cys Thr Asp Leu Pro Pro Gln Lys Lys Lys
625                 630                 635
```